United States Patent [19]

Banes

[11] Patent Number: 4,789,601
[45] Date of Patent: Dec. 6, 1988

[54] BIOCOMPATIBLE POLYORGANOSILOXANE COMPOSITION FOR CELL CULTURE APPARATUS

[76] Inventor: Albert J. Banes, 2021 Bivins Rd., Durham, N.C. 27712

[21] Appl. No.: 46,440

[22] Filed: May 4, 1987

[51] Int. Cl.$^4$ ............................................. C08G 77/04
[52] U.S. Cl. ................................. 428/447; 428/116; 428/178; 435/287; 524/17; 524/588
[58] Field of Search ....................... 428/116, 447, 178; 435/287, 300, 301; 524/17, 588

[56] References Cited

U.S. PATENT DOCUMENTS

| | | | |
|---|---|---|---|
| 3,350,349 | 10/1967 | Hyde | 525/477 X |
| 3,867,549 | 2/1975 | Costello et al. | 514/773 X |
| 4,070,224 | 1/1978 | Zemlin et al. | 428/447 X |
| 4,273,834 | 6/1981 | Yokokura et al. | 428/35 X |
| 4,483,901 | 11/1984 | Okita et al. | 428/447 X |
| 4,695,547 | 9/1987 | Hilliard et al. | 435/289 X |
| 4,701,017 | 10/1987 | Kookootsedes et al. | 428/447 X |
| 4,705,810 | 11/1987 | Millet et al. | 521/92 X |
| 4,735,778 | 4/1988 | Maruyama et al. | 422/102 |

OTHER PUBLICATIONS

Leung, D. Y. M. et al., "A New in Vitro System for Studying Cell Response to Mechanical Stimulation", Experimental Cell Research, 109, (1977) 285-298.
Banes, A. J. et al., "A New Vacuum-Operated Stress-Providing Instrument that Applies Static or Variable Duration Cyclic Tension or Compression to Cells in Vitro", J. Cell Sci., 1985.
Somjen, D. et al., "Bone Remodelling Induced by Physical Stress in Prostaglandin $E_2$ Mediated", Biochimica et Biophysica Acta, 627, (1980) 91-100.
Brunette, D. M. et al., "Mechanical Stretching Increases the Number of Epithelial Cells Synthesizing DNA in Culture", J. Cell Sci., 69, (1984) 35-45.
Hasagawa et al., "Mechanical Stretching Increases the Number of Cultured Bone Cells Synthesizing DNA and Alters Their Pattern of Protein Synthesis", Calcif Tissue Int., 37, (1985) 431-436.
Leung, D. Y. M. et al., "Cyclic Stretching Stimulates Synthesis of Matrix Components by Arterial Smooth Muscle Cells in Vitro", Science, 191, (1976) 475-477.

Primary Examiner—Henry F. Epstein
Attorney, Agent, or Firm—Webb, Burden Ziesenheim & Webb

[57] ABSTRACT

A polyorganosiloxane composition having a biocompatible surface thereon is disclosed. The biocompatible surface results from the derivatization, or amination, of the surface intended for cell contact. More specifically, the present invention is a polyorganosiloxane composition in which the surface is either treated with a primary amine and optional peptide or the surface is co-cured with a primary amine-containing silane or siloxane. The aminated polyorganosiloxane has utility as a cell culture substrate or in a variety of artificial organ applications such as brest implants, synthetic blood vessels, joints, tendons and heart valves. A vacuum apparatus for use with specialized cell culture plates incorporating the biocompatible polyorganosiloxane composition is also disclosed.

25 Claims, 3 Drawing Sheets

BIOCOMPATIBLE POLYORGANOSILOXANE COMPOSITION FOR CELL CULTURE APPARATUS

FIELD OF THE INVENTION

The present invention relates to surface-modified polyorganosiloxane compositions which demonstrate improved biocompatibility both in vitro and in vivo, and to a cell culture apparatus incorporating such compositions.

BACKGROUND OF THE INVENTION

Although the use of synthetic polymers in technology and in everyday life is widespread, the use of polymers in clinical and laboratory medicine has been cautious and limited. This restricted use is unrelated to need; suitable synthetic polymers are increasingly in demand for use in the fabrication of artificial organs and membranes for hemodialysis or oxygenation, in the preparation of plasma or blood substitutes, and in the manufacture of implanted or soluble polymers as substrates for the slow release of drugs, hormones or other physiologically-active agents.

Unfortunately, even those synthetic polymers which demonstrate relatively low cytotoxicity, such as the various silicone resins, typically demonstrate at least some degree of bioincompatibility. For example, a silicone resin implant embedded within mammalian or human tissue ordinarily eventuates encapsulation of that implant, including epithelial encapsulation or thickening and/or keratinization of the surrounding connective tissues. A similar phenomenon in vitro prevents cells from adhering to many synthetic polymer substrates when those substrates are subjected to elongation or other stresses.

With respect to in vitro cell cultures, specifically, there is as great a need for elastomeric substrates to which cells can adhere in vitro as there is a need for biocompatible polymers for in vivo applications. This need arose from developments in the area of in vitro flexing of cell cultures, which flexing techniques offer certain advantages over conventional cell culture methods.

Conventional culture plates or bottles used for the propogation of cells in vitro are typically manufactured from polystyrene or glass. The routine method for culturing cells includes inoculating the cells into flasks, single culture dishes or multi-well plates, adding a nutrient medium and incubating the cells under controlled conditions. Alternative methods for the in vitro culturing of cells include growing cells in continuously rolling glass or plastic bottles, so that the cells adhere to the wall of a culture vessel beneath continually rotated medium (cells may alternately be grown in fluted roller bottles that have increased inside surface area), or culturing cells on glass or complex polysaccharide beads, tissue segments or in suspension in a suitable culture medium. With all these methods, however, the culture medium does not exert any deforming stress upon the cells themselves such as would simulate the in vivo stresses applied by tendons, for example, or the cyclic stresses exerted by the heart or lungs on their constituent cells.

To simulate what cells experience in the way of physical deformation in the environment of the lung, cells can be adhered to and grown upon an elastomeric substrate which is cyclically stretched to 20 percent elongation, fifteen times a minute, in order to simulate a resting situation. Lung cells may also be cyclically stretched at 20 percent elongation, 40 times a minute, to simulate an exercise period. Such research may be tailored to address such questions as whether cells are more susceptible to viral infection when they are cyclically stretched or at rest, or whether macrophages phagocytose bacteria more readily if they are subjected to cyclic deformation, and related questions. The answers to these questions can then be considered in the development of treatment plans for patients having viral or bacterial infections.

One system for the in vitro flexing of cells in culture is documented in Banes, A. J. et al., "A New Vacuum-Operated Stress-Providing Instrument That Applies Static or Variable Duration Cyclic Tension or Compression to Cells In Vitro," *J. cell Sci.*, 1985. In that published protocol, however, physical limitations of the plastic (polystyrene) Petri dish precluded more than a limited amount of cyclic deformation in the cell substrate (Petri dish base). (Related in vitro systems are documented in Somjen, D. et al., "Bone Remodeling Induced by Physical Stress in Prostaglandin $E_2$ Mediated," *Biochimica et Biophysica Acta*, 627 (1980) 91–100; Leung, D. Y. M. et al., "A New In Vitro System for Studying Cell Response to Mechanical Stimulation," *Experimental Cell Research*, 109 (1977) 285–298; Leung, D. Y. M. et al., "Cyclic Stretching Stimulates Synthesis of Matrix Components by Arterial Smooth Muscle Cells In Vitro," *Science*, 191 (1976) 475–477; Hasagawa et al. "Mechanical Stretching Increases the Number of Cultured Bone Cells Synthesizing DNA and Alters Their Pattern of Protein Synthesis," *Calcif Tissue Int*, 37 (1985) 431–436; and Brunette, D. M. et al., "Mechanical Stretching Increases the Number of Epithelial Cells Synthesizing DNA in Culture," *J. Cell Sci*, 69 (1984) 35–45.

In view of all of the above, a need remains for a low cytotoxicity synthetic polymer composition which does not promote encapsulation in vivo or cellular nonadherence in vitro. Ideally, such a composition would also offer the various benefits of the silicone resin compositions which are generally known to demonstrate both low cytotoxicity and high tensile and flexural strength.

SUMMARY OF THE INVENTION

In order to meet this need, the present invention is a polyorganosiloxane composition having a biocompatible surface thereon. The biocompatible surface results from the derivatization of the surface intended for cell contact. More specifically, the present invention is a polyorganosiloxane composition in which the surface is embedded with carbon particles, or is treated with a primary amine and optional peptide, or is co-cured with a primary amine- or carboxyl-containing silane or siloxane. The derivatized polyorganosiloxane has utility as a cell culture substrate or in a variety of artificial organ applications such as breast implants, synthetic blood vessels, joints, tendons, heart valves and the like. A vacuum apparatus for use with specialized cell culture plates incorporating the biocompatible polyorganosiloxane composition is also disclosed.

DETAILED DESCRIPTION OF THE INVENTION

Figure 1:
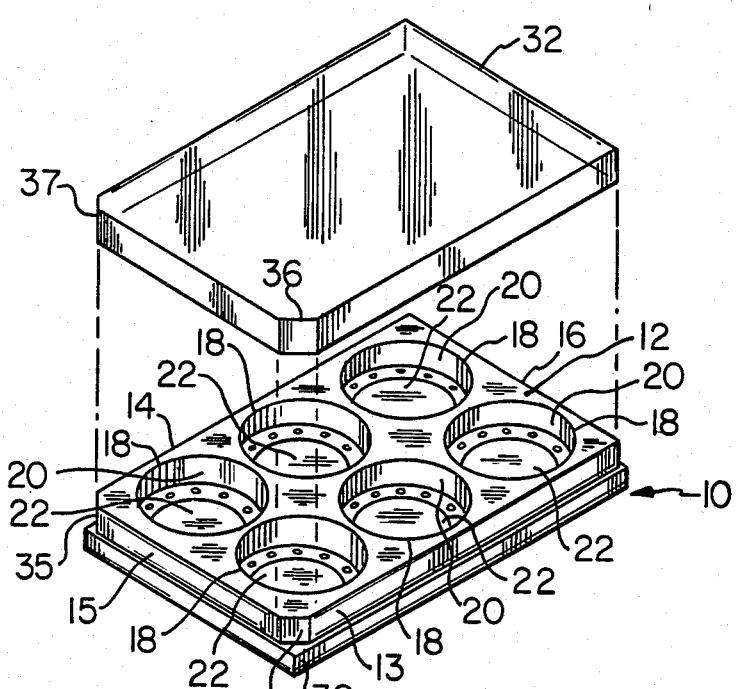
FIG. 1 is an exploded perspective view of a six-well culture plate containing a biocompatible polyorganosiloxane composition according to the present invention and a cover therefore.

The surface modification of the polyorganosiloxane compositions according to the present invention is accomplished by one or more of three methods. The composition surface may be embedded with carbon particles, may be treated with a primary amine and optional peptide, or may be co-cured with a primary amine- or carboxyl-containing silane or siloxane. It is believed that, when present, the amino or carboxyl groups and optional peptides orient to the surface of the polyorganosiloxane composition and provide the biocompatible surface. The derivatization reaction may be carried out on the surface of either an uncured or a cured polyorganosiloxane. In every case, however, derivatization is conducted on the surface of the polyorganosiloxane.

A first method for the derivatization of a cured or uncured polyorganosiloxane surface, such as a membrane, comprises embedding the surface with a plurality of elemental carbon particles. For example, the uncured surface may be suspended over a bunsen burner flame both to deposit fine elemental carbon particles on and to cure said surface. The resulting surface demonstrates improved biocompatibility.

The second method for the derivatization of a cured polyorganosiloxane membrane comprises an amination method which includes two basic steps. First, the membrane surface is treated for 30 minutes under ambient conditions, with swirling, with between 0.5 and 1 ml. 1N. HCl for each $cm^2$ of its surface area. The acid is then decanted. The surface is then contacted, for 30 minutes and again under ambient conditions, with between 0.5 and 1 ml. 1M. $NH_4OH$ per $cm^2$ surface. In the alternative, after the acid is decanted the surface may be exposed to ammonia vapor for 15 minutes in a bell jar. The resultant modified surface is washed with water and permitted to dry. Other acids and primary amines may be substituted in stoichiometrically equivalent amounts, such as HFl, HBr (or other halide containing acids) $NH_4Cl$ or $NH_4HCO_3$. It is believed that the surface thus treated demonstrates biocompatibility due to the presence of amino groups pendant from the treated polyorganosiloxane and oriented to the polymer surface.

A third method for treating polyorganosiloxane surfaces includes the amination treatment described above followed by an optional peptidation. After the acidification and amination steps, followed by water washing, the surface is treated by contacting it with between 0.5 and 1 ml. 1 millimolar to 1 nanomolar glutaraldehyde per $cm^2$. Reactive equivalent amounts of other aldehydes, such as acetaldehyde or butyraldehyde may be substituted. The glutaraldehyde-treated surface is then contacted with an aqueous peptide which typically has both amine and carboxyl functionalities. Ordinarily, the peptide selected will have between 2 and 40 amino acids in linear configuration so as to provide amine and carboxyl functionality at opposing terminal ends of the peptide. However, larger peptides and proteins having molecular weights of several thousand may also be used. A final water wash follows. It is believed that the aldehyde creates a Schiff's base in reaction with the bound amine, leaving a free aldehyde which then reacts with the amino group of the peptide. The resultant aminated/peptidated polyorganosiloxane therefore provides a biocompatible primary amine-containing carboxyl-terminated surface, which biocompatibility is particularly enhanced when the peptide is selected for its histocompatibility with the specific cell culture. For any given application, peptide compatibility may be determined by means known in the art.

A fourth method of amination comprises the co-curing of a polyorganosiloxane with a primary amine- or carboxyl-containing silane or siloxane. (The term "co-curing" signifies that at least one of the adjacent silane- or siloxane-containing compositions is cured in situ.) Exemplary compounds include 3-aminopropyltriethoxysilane, 2-aminoethyltrimethoxysilane, trimethylsilylformic acid, 3-(trichlorosilyl) butanoic acid, and 1,1,1-trichloro-N-(trimethylsilyl) silanamine. Suitable diluents for the primary amine- or carboxyl-containing silane or siloxane include methoxy trimethylsilane, trimethoxysilane, chlorodimethylsilane and chlorotriisocyanatosilane. The silane or siloxane (with or without silane diluent) is applied in aqueous solution or in aqueous buffer solution at substantially neutral to basic pH to cover a cured polyorganosiloxane surface in entirety. Any of the buffers ordinarily used in the preparation of cell culture media are suitable for use as the solvent or carrier for the silane or siloxane such as, for example, the 20 mM HEPES buffer well known in the art. The resultant layers are co-cured at room temperature for a period of not less than 15 minutes nor more than twenty-four hours. Curing may be effected at elevated temperatures if desired. The primary amine- or carboxyl-containing silane or siloxane may alternatively be coated onto the uncured polyorganosiloxane, with the subsequent co-curing of the two layers in the same manner as would have been chosen for the curing of the base polyorganosiloxane layer alone. The cured surfaces may be further treated with the optional peptidation or carbon particle embedding treatment described above.

After preparation is complete by any one of the above methods, the composition is washed with water or buffer, sterilized such as with ultraviolent light, and packaged for storage prior to use. Other means of sterilization include microwave energy, gamma radiation and other sterilization means known in the art.

Specific derivatization methods are illustrated with particularity in the Examples, infra.

Biocompatible derivatized polyorganosiloxanes in accordance with the methods described above have a vast number of potential applications, but one particularly important use for such elastomers is in the in vitro flexing of cell culture substrates. Even as cell culture substrates, the use of the derivatized polyorganosiloxanes of the present invention are limitless: the compositions may be used alone, in combination with a wide variety of cell culture vessels, or in any other application in which adherent cell culture growth is desired.

Figure 2:
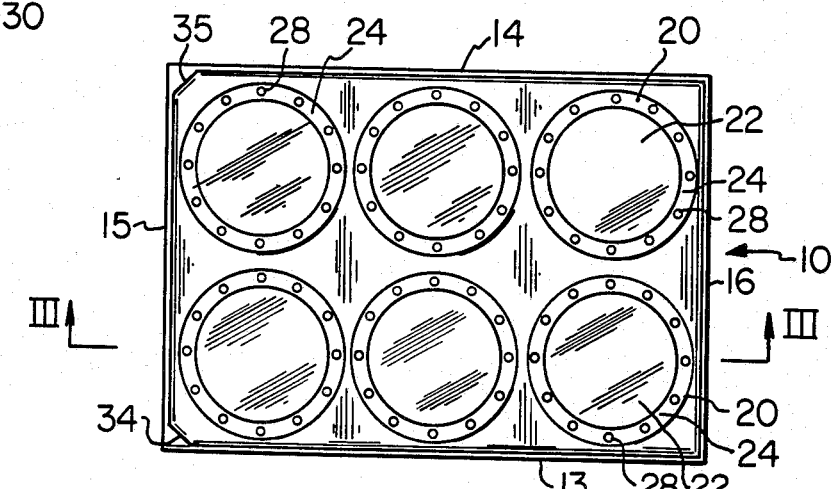
FIG. 2 is plan view of the culture plate illustrated in FIG. 1.
Figure 3:
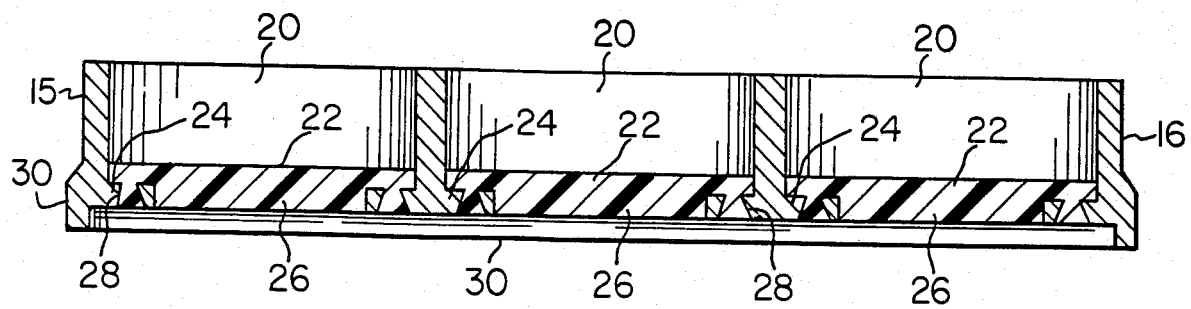
FIG. 3 is a section taken along lines III—III in FIG. 2.

One embodiment of a cell culture plate 10, utilizing the biocompatible polyorganosiloxane compositions of the present invention, is shown in FIGS. 1–3. The culture plate 10 is a substantially flat, rectangularly shaped structure including a flat upper surface 12, and side walls 13, 14 and end walls 15, 16 extending downwardly from the outer edges of the upper surface 12 and joined together along adjacent edges. A plurality of open topped wells 18 extend downwardly from the upper surface 12. While the culture plate 10 shown in FIGS. 1–3 includes six wells 18 in a two by three array, it is to be understood that any number of wells 18, even as few as one, may be included as desired.

Each well 18 includes a cylindrically shaped side wall 20 and terminates in a substantially flat well base 22 attached to side wall 20. The well base 22 includes an anchor ring 24 integral with the side wall 20. The remainder of the well base 22 is formed by an elastomeric membrane 26 which both covers the anchor ring 24 and fills the opening defined by the anchor ring 24. The anchor ring 24 may include a plurality of holes 28, preferably frustoconically shaped, extending therethrough. The holes 28 are filled with elastomeric material continuous with the elastomeric membrane 26, which structure aids in securing the membrane 26 in place in the well base 22. The membrane 26 is fabricated from a surface-modified polyorganosiloxane composition as described above.

The wells 18 extend downwardly to an extent slightly below the lower edge of side walls 13, 14 and end walls 15, 16. The culture plate 10 includes a protective base rim 30 which extends downwardly from the lower edges of side walls 13, 14 and end walls 15, 16 and beyond the bottom surface of the well bases 22. The base rim 30 functions to elevate, and to prevent any scratching of or damage to, the well bases 22.

The upper surface 12 of the culture plate, and hence the plurality of wells 18, may be closed off by a cover 32 or the like. The corners between adjacent end walls and side walls may be configured to enable consistent orientation of the culture plate. As shown in FIGS. 1 and 2, corner 34 between side wall 13 and end wall 15 and corner 35 between side wall 14 and end wall 15 are beveled. The cover 32 also has correspondingly beveled corners 36 and 37. The outer surface of the base rim 30 may be grooved to provide for more secure handling of the culture plate 10.

The culture plate 10 shown in FIGS. 1–3 may be manufactured from a commercially available Falcon six-well culture plate formed of 1.5 mm thick polystyrene. The Falcon culture plate includes a well base formed of a solid layer of substantially planar polystyrene. The well base of the Falcon culture plate can be partially excised, leaving a base anchor ring 24 of polystyrene in each well 18. A plurality of frustoconical holes 28 are drilled into each anchor ring 24, with the narrow end of the hole at the upper surface of the anchor ring 24. A suitable release layer is affixed just beneath the anchor rings 24 by means known in the art, and an uncured polyorganosiloxane composition is deposited within each well 18. One example of a suitable polyorganosiloxane composition is the Dow-Corning MDX4-4210 (sold under the trademark SILASTIC ®); an exemplary formulation is 85 parts Dow-Corning MDX4-4210, 15 parts of the matching lot number catalyst and 15 parts medical grade silicone oil. The uncured polyorganosiloxane which results from such or a similar admixture is poured, in predetermined amounts, into each well 18 to form a membrane in the bottom thereof, and at the same time the uncured composition flows into each of the frustoconical holes 28 in the anchor ring 24. The polyorganosiloxane may then be deaerated, cured and the release layer removed to yield the culture plate 10 of FIGS. 1–3.

Deaeration of, or removal of air bubbles from, the uncured polyorganosiloxane is particularly important in the preparation of an optically clear well base 22. (Optical clarity facilitates microscopic examination of the elastomer bearing cell culture, for example.) Air bubbles may be removed by means known in the art or may specifically be removed by a specialized centrifuging technique. In order to deaerate by centrifugation, the individual culture plates 10 with or without their covers 32 are placed in centrifuge receptacles adapted to receive them. The plates are then subjected to centrifugation at 800–1200 times gravity for 3–6 minutes. The plates 10 are removed from the centrifuge, are rotated or "rocked" by hand or machine to equilibrate the polyorganosiloxane well base 22 to as close to a flat membrane as possible, the plates are cured in an oven at approximately 60° C. for 45 minutes and, upon removal from the oven and cooling, the release layer is removed. The upper surfaces of the well bases 22 of the culture plate 10 may then be derivatized by any of the methods described above and as described with particularity in the Examples, infra.

In general, the culture plate 10 in accordance with the present invention provide well bases 22 which, in addition to providing a substrate to which cells can adhere, may be elongated or otherwise stressed by a number of means. One particularly convenient method for elongating an elastomeric cell substrate such as the well base 22 includes selectively subjecting an enclosed area immediately beneath the well base 22 to a controlled vacuum source. Such vacuum elongation might be accomplished by individual vacuum ports affixed beneath each well base 22. A simpler yet more effective apparatus for subjecting each well base 22 to selective vacuum is illustrated in the vacuum apparatus of FIGS. 4–6.

Figure 4:
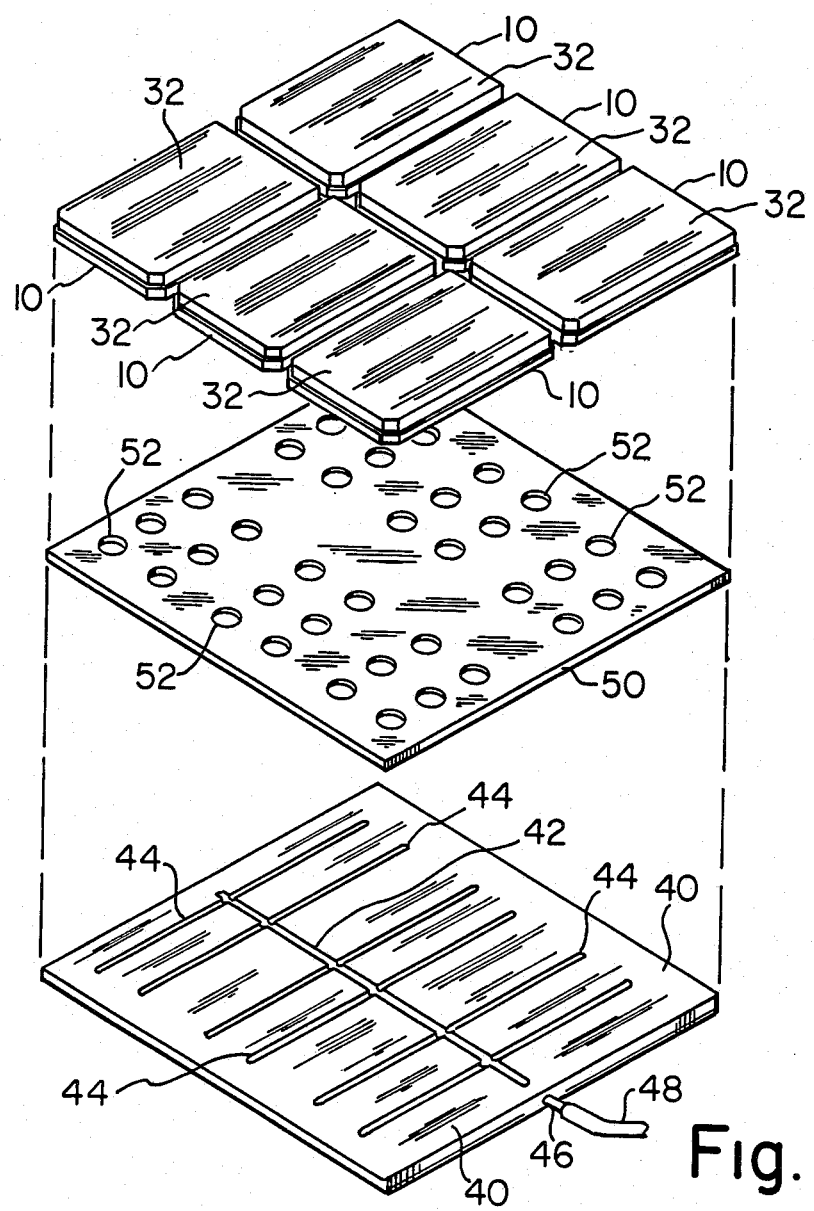
FIG. 4 is an exploded perspective view of a vacuum apparatus suitable for use in association with the culture plate shown in FIG. 1.
Figure 6:
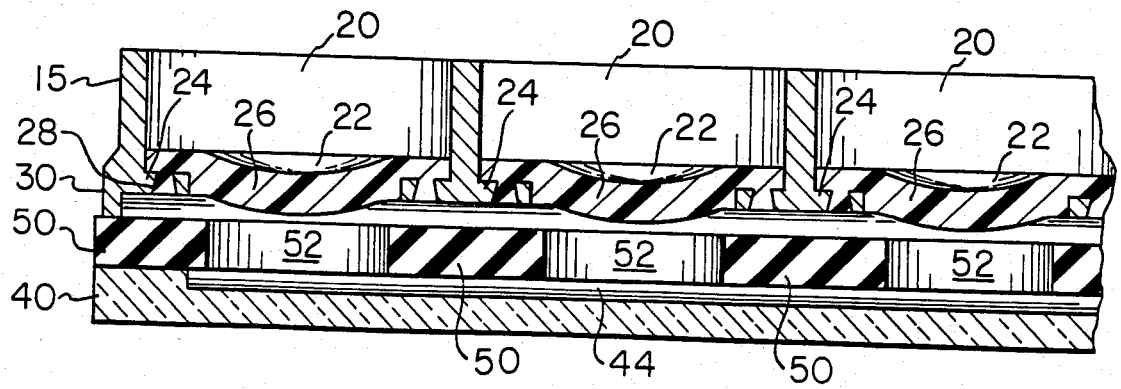
FIG. 6 is a section taken along lines VI—VI in FIG. 5.
Figure 5:
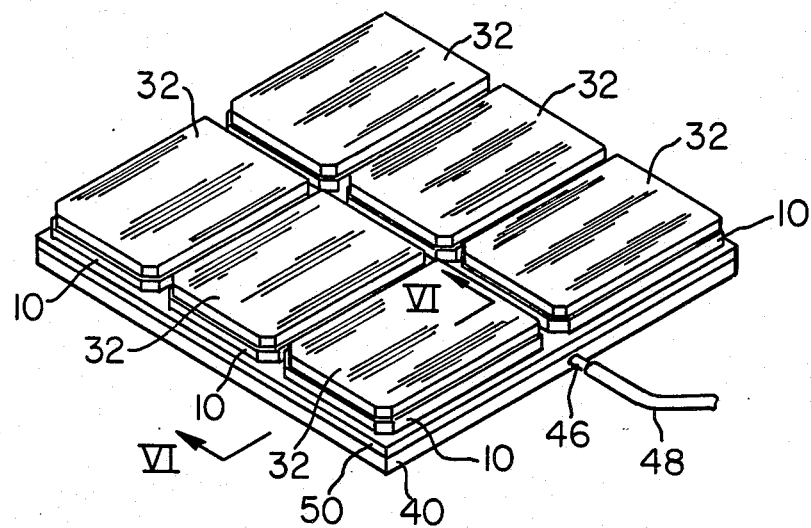
FIG. 5 is a perspective view of the vacuum apparatus of FIG. 4.

The vacuum apparatus shown in FIGS. 4–6 includes a vacuum plenum 40 formed from a solid, flat, rectangular sheet of Plexiglas TM or the like. The upper surface of the plenum 40 has a plurality of vacuum channels cut therein and having a depth less than the thickness of the plenum 40. A main vacuum channel 42 extends down the middle of the plenum 40 substantially along its entire length. A plurality of side vacuum channels 44 extend perpendicularly from each side of the main vacuum channel 42 and are in fluid communication therewith. A hole is drilled through one end of the plenum 40 and is fitted with a nipple 46 which is in fluid communication with the main vacuum channel 42. The nipple 46 is adapted to receive a vacuum hose 48 which connects the plenum 40 to a source of vacuum (not shown).

Each vacuum channel 42, 44 is open to the upper surface of the plenum 40 at every point along its length. In order to close off the open topped vacuum channels 42, 44, a flat, gum rubber gasket 50 is positioned adjacent the upper surface of the plenum 40. The gasket 50 is rectangularly shaped and has the same approximate dimensions as the plenum 40. The gasket 50 includes a plurality of openings or apertures 52 therethrough which are in fluid communication with the underlying side vacuum channels 44. The main vacuum channel 42 is completely covered by the gasket 50. The apertures 52 are positioned so that each will align with and be located immediately beneath the base 22 of one well 18 when a culture plate 10 is positioned on the upper surface of the gasket 50. Therefore, the apertures 52 create individual sealed air chambers which are accessible only through the vacuum channels 42, 44. In the embodiment shown in FIGS. 4-6, the gasket 50 includes six, two by three arrays of apertures 52. Each group of three apertures 52 is located above a separate side vacuum channel 44. Therefore, the vacuum apparatus shown in FIGS. 4-6 will accommodate six of the culture plates 10 described above and shown in FIGS. 1-3. While the vacuum apparatus shown in FIGS. 4-6 is designed for the use of six individual six-well culture plates, it is to be understood that any number of individual plates, having a variety of number of wells, can be used by merely providing the vacuum channels 42, 44 and apertures 50 in the location required by the particular plate or plates used.

Any vacuum induced through the vacuum hose 48 will likewise be induced, via the vacuum channels 42, 44, in each chamber formed by the aperture 52 beneath the well base 22 of the culture plate 10. As the vacuum is induced, the elastomeric membrane 26 in each well 18 will be pulled downwardly and begin to stretch to a cured configuration. FIG. 6 shows the downward elongation of the elastomeric membrane 26 when the vacuum is fully applied. As the vacuum is reduced, the membrane 26 returns to the original, horizontal configuration shown in FIG. 3. The vacuum elongation of the membrane 26 may be constant or cyclic, or may be irregular or applied in a pattern as desired. Each of the six culture plates 10 will, however, be subjected to the identical vacuum conditions.

Figure 7:
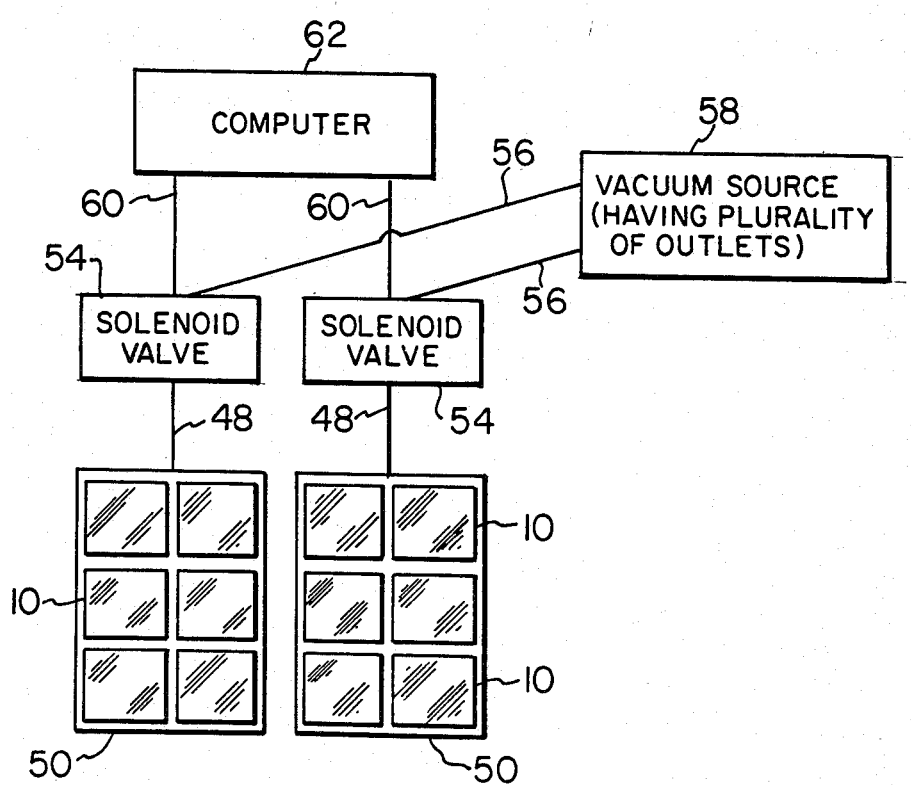
FIG. 7 is a schematic diagram of an apparatus for regulating the vacuum apparatus of FIG. 3.

The vacuum apparatus shown in FIGS. 4 and 5 may be subjected to controlled application of vacuum by a wide variety of systems. One such system is shown in schematic in FIG. 7. Each vacuum apparatus, including the plenum 40 (not visible), gasket 50 and culture plates 10, is connected via hose 48 to a solenoid valve 54. The solenoid valves 54 are each connected via hose 56 to a source of vacuum 58 having a plurality of outlets. The solenoid valves 54 are each connected via wire 60 to a computer 62 or other control apparatus. Each solenoid valve 54 will control the application of vacuum to the elastomeric membranes 26 in the well base 22 of each culture plate 10. The computer 62 is used to control the operation of the solenoid valves 54 not only to control the timing and intensity of the vacuum supplied, but also to equilibrate the channels 42, 44 in the vacuum plenum 40 and permit the return of ambient air as desired. Either a single solenoid valve 54 or a plurality of valves 54 may be used to accomplish both vacuum induction and return to ambient pressure. In addition, a pressure transducer may be associated with each vacuum plenum, or may be positioned beneath each elastomeric membrane 26, with its output signal supplied to the computer 62. The information developed by the pressure transducer may be used to control the actual vacuum applied.

Cells adhering to the well base 22 are subjected to commensurate stress as is applied to the well base 22 itself. The system may thus be used for the in vitro flexing of cell culture substrates as discussed above. The six culture plates 10 and associated vacuum apparatus may, of course, be incubated in a standard incubator or may otherwise be subjected to culturing conditions as would any multi-well culture plate known in the art.

For specific applications which do not require flexing of the cells but for which adherence of the cells to the cell substrate is desired, a surface-modified polyorganosiloxane composition according to the present invention may alternatively be deposited in a six-well culture plate without first excising the well bases. The deposited surface-modified polyorganosiloxane layer may be made of any thickness, but ordinarily membranes on the order of one millimeter are all that is required.

A variety of modifications may be made to the subject disclosure without changing its nature. Six-well culture plates prepared with base anchor rings need not have base anchor ring holes 28; for example, the base anchor ring 24 can be roughened prior to deposition of the uncured polyorganosiloxane so that the adherence of the siloxane resin to the actual base anchor ring surface is enhanced. The surface-modified polyorganosiloxane may likewise be incorporated as the cell culture substrate in any number of cell culture vessels and is not limited in any way to multi-well plates. The polyorganosiloxane compositions of the present invention may likewise be used on the sides of culture vessels as individual discrete particles or beads to which cells can adhere, or in any of a number of other ways that will be immediately evident to one skilled in the art. Vacuum elongation may be induced in the polyorganosiloxane membranes prepared as described above by any system for applying vacuum. Thickness of layers or membranes as prepared may be controlled by known means to yield a substrate having predictable elongation characteristics.

Because it is believed that the present surface-modified polyorganosiloxane compositions do not promote epithelial encapsulation or thickening and/or keratinization of the surrounding connective tissues, virtually any implant or artificial organ to which cell adherence is desired may be fabricated from the present polyorganosiloxane composition. Potential uses for the surface-modified polyorganosiloxanes include, but are not limited to, synthetic blood vessels, structural prothesis including breast implants, and synthetic joints such as knees or knuckles. For example, synthetic knuckles may be fabricated from a polyorganosiloxane that is selectively aminated at the knuckle structure ends so that cells can attach to the end portions of the knucle, which anchor in bone, but do not adhere to the central knuckle area where gliding must occur. Selectively derivatized polyorganosiloxanes in this manner are especially suited for use as implants because cell adherence and nonadherence may be selectively controlled.

The present invention is described with greater particularity in the Examples below.

EXAMPLE 1

A 5×3 5/16 inch Falcon six-well polystyrene culture plate was immobilized in a wooden jig holder. The center point of the bottom of each well was marked. A 1-1/16 inch metal drill bit was positioned immediately over the centered mark and the drill bit was used to drill almost completely through the plastic. Drilling completely through was avoided to prevent the hole from becoming oversized. The central portion of the well was pushed out using finger pressure, leaving a 4 mm. wide anchor rim at the base of the well.

The plates were inverted in the jigs and secured. Twelve evenly-spaced frustoconical holes were drilled down into the remaining polystyrene base of the well with a grinding bit. The plate was inverted in the jig once again, and a stone bit was used to roughen the remaining polystyrene ring at the base of the well as well as the side walls of the well. Plastic particulates were thereafter vacuumed away.

Subsequent to a 95% ethanol wash of the entire culture plate, to remove contaminants introduced by handling, the plate was inverted onto a clean surface and the well bottoms were sealed with three inch adhesive tape. The adhesive tape was applied carefully so as to create a smooth, flat bottom to each culture plate well. The plates were inverted to an upright position.

A polyorganosiloxane composition was prepared by admixing 85 g. Dow-Corning MDX4-4210 clean grade elastomer with 15 g. of the accompanying catalyst and 15 g. of medical grade silicone oil. The components were weighed out in a plastic disposable beaker and were admixed thereafter using the paint mixing bit of a drill assembly. Two 60 cc. plastic syringes were filled with the resultant admixture, and the remainder of the admixture was stored at −20° C. for later use.

Working quickly, each plate was placed on a balance and the syringes were used to add 2.0 g. of the mixture to each well. After four plates were poured, all four plates were placed in a centrifuge and were centrifuged at 1,000 times gravity for 4.5 minutes (at ambient temperature) to remove all the visually detectable air bubbles from the resin. As a result of working quickly, the resin did not become appreciably more viscous between dispensing and centrifugation, and the membranes in the bases of each culture plate well settled readily to form a flat surface after removal from the centrifuge.

To cure the plates, the plates were placed on a flat metal rack in an oven set at 60° C. for 45 minutes. (Had curing at elevated temperature been delayed for some reason, the centrifuged plates could have been stored at −20° C. prior to heat processing.) The plates were then removed from the oven and were permitted to equilibrate to room temperature on a flat surface for 30 minutes.

Five milliliters of 98% pure 3-aminopropyltriethoxysilane were admixed in five milliliters of 1M. HEPES buffer, pH 7.2, with subsequent addition of deionized water to a final volume of 250 ml. Three milliliters of the resultant 3-aminopropyltriethoxysilane solution were then added to each well and the culture plates were covered with polyethylene film. The plates were incubated at room temperature in the dark for 12 hours. The resultant aminated polyorganosiloxane surfaces at the base of each cell culture well were then rinsed briefly in 2 washes of 20 mM HEPES buffer, followed by a final application of HEPES buffer, which was left in place on the aminated surface for 15 minutes. The adhesive tape was then carefully removed from the base of the plates; the resultant culture plates were sterilized in ultraviolet light in a cell culture hood for 12 hours, and the sterilized plates were hermetically sealed under sterile conditions in a plastic overwrap.

EXAMPLE 2

The culture plates prepared in accordance with Example 1 were inoculated and incubated in association with the vacuum apparatus illustrated in FIGS. 4-7, which cyclically elongated each well base twenty percent at the rate of 40 times a minute. After cell culturing was complete, the optically clear biocompatible polyorganosiloxane membrane permitted microscope examination of the cells without the removal of the cells from the elastomeric substrate. The elastomeric substrate also proved suitable for sampling, and was successfully cut with each of a knife, a cork borer and a trephine punch. These cut segments having cells attached were mounted on slides, stained with fluorescent reagents and were examined under a microscope.

EXAMPLE 3

The process according to Example 1 was repeated except that as a substitute for centrifugation, the plates were incubated at −20° C. for five days so that the elastomer was deaerated slowly and the resin flattened on its own. The plates were then removed from the freezer and were cured and aminated in accordance with Example 1.

EXAMPLE 4

Biocompatible polyorganosiloxane composition well bases were prepared in accordance with Example 1, except that amination proceeded by the following method. Each cured polyorganosiloxane well base was contacted with 1 ml. 1N. HCl, followed by an addition of 1 ml. 1M. NH$_4$OH. Each reagent was left in place for 30 minutes and was decanted thereafter. The plates were then washed in water, permitted to dry, and were sterilized and wrapped in accordance with Example 1.

EXAMPLE 5

Biocompatible polyorganosiloxane composition well bases were prepared in accordance with Example 4, except that after the NH$_4$OH addition and water washing, the well bases were treated with glutaraldegyde and peptide as follows.

One ml. 1 nanomolar glutaraldehyde was added to each well. Each well was then contacted with an aqueous peptide having both amine and carboxyl functionality. Enough of the aqueous peptide was added to cover the well base surface. The peptide selected was 1 mM NH$_2$—RGDS—COOH (R=arginine, G=glycine, D=aspartic acid and S=serine) in water. After one-half hour, the plates were washed, dried, sterilized and wrapped in accordance with Example 1.

Although the invention has been described with respect to particular embodiments and methods thereof, the invention is to be limited only insofar as is set forth in the accompanying claims:

I claim:

1. A biocompatible resin, comprising: a polyorganosiloxane composition having incorporated at the surface thereof a substance selected from the group consisting of an amine, a carboxylic acid, or elemental carbon.

2. The biocompatible resin according to claim 1, wherein said substance is an amine and said amine is a primary amine.

3. The biocompatible resin according to claim 1, wherein said polyorganosiloxane composition further has a peptide incorporated at the surface thereof.

4. The biocompatible resin according to claim 3 wherein said peptide further comprises a carboxyl-terminated peptide.

5. The biocompatible resin according to claim 4 wherein said carboxyl-terminated peptide has amine functionality.

6. The biocompatible resin according to claim 5, wherein said carboxyl-terminated peptide is incorporated at the surface of said polyorganosiloxane by means of its amine functionality.

7. A biocompatible resin, comprising: a polyorganosiloxane composition having co-cured at the surface thereof a composition selected from the group consisting of: primary amine-containing silanes, carboxyl-containing silanes, primary amine-containing siloxanes and carboxyl-containing siloxanes.

8. The biocompatible resin according to claim 7 wherein said composition co-cured with said polyorganosiloxane composition is selected from the group consisting of: 3-aminopropyltriethoxysilane, 2-aminoethyltrimethoxysilane, trimethylsilylformic acid, 3-(trichlorosilyl) butanoic acid, and 1,1,1-trichloro-N-(trimethyisilyl) silanamine.

9. A cell culture substrate comprising: solid means for supporting a cell culture having at least one surface further comprising a polyorganosiloxane composition having incorporated at the surface thereof a substance selected from the group consisting of an amine, a carboxylic acid, or elemental carbon.

10. A cell culture substrate according to claim 9 wherein said substance is an amine and said amine is a primary amine.

11. The cell culture substrate according to claim 9 wherein said polyorganosiloxane composition further has a peptide incorporated at the surface thereof.

12. The cell culture substrate according to claim 11 wherein said peptide further comprises a carboxyl-terminated peptide.

13. The cell culture substrate according to claim 12 wherein said carboxyl-terminated peptide has amine functionality.

14. The cell culture substrate according to claim 9, wherein said carboxyl-terminated peptide is incorporated at the surface of said polyorganosiloxane by means of its amine functionality.

15. The cell culture substrate according to claim 9 wherein said polyorganosiloxane composition is a polyorganosiloxane composition having co-cured at the surface thereof a composition selected from the group consisting of primary amine-containing silanes, carboxyl-containing silanes, primary amine-containing siloxanes and carboxyl-containing siloxanes.

16. The cell culture substrate according to claim 15 wherein said composition co-cured with said polyorganosiloxane composition is selected from the group consisting of 3-aminopropyltriethoxysilane, 2-aminoethyltrimethoxysilane, trimethyisilyiformic acid, 3-(trichlorosilyl) butanoic acid, and 1,1,1-trichloro-N-(trimethylsilyl) silanamine.

17. A cell culture substrate comprising: solid means for supporting a cell culture having at least one surface further comprising a polyorganosiloxane composition having a surface treated by co-curing therewith an adjacent layer containing a compound selected from the group consisting of primary amine-containing silanes, carboxyl-containing silanes, primary amine-containing siloxanes and carboxyl-containing siloxanes.

18. The cell culture substrate in accordance with claim 17 wherein said polyorganosiloxane composition is treated by co-curing therewith an adjacent layer of a compound selected from the group consisting of 3-aminopropyltriethoxysilane, 2-aminoethyltrimethoxysilane, trimethylsilylformic acid, 3-(trichlorosilyl) butanoic acid, and 1,1,1-trichloro-N-(trimethylsilyl) silanamine suspended in an aqueous or aqueous buffer carrier, by maintaining the adjacent compositions at about room temperature, substantially in the absence of light for about twenty-four hours.

19. The cell culture substrate in accordance with claim 17 wherein said co-curing is effected at about 60° C. and ambient pressure over a period of about 45 minutes.

20. The cell culture substrate according to claims 9 or 17 wherein said solid means is a multi-well polystyrene plate.

21. The cell culture substrate according to claim 20 wherein each of said wells contains said polyorganosiloxane composition at a well base thereof.

22. A cell culture substrate according to claim 21 wherein said polyorganosiloxane composition forms a laminate with the well base of each of said wells.

23. The cell culture substrate according to claim 21 wherein substantially all the well base of each of said wells comprises a single layer of said polyorganosiloxane composition.

24. The cell culture substrate according to claim 23 wherein said polyorganosiloxane composition is adhered to an anchor ring at the base of each of said wells.

25. A cell culture substrate comprising a cell culture plate having one or more wells therein, each of said wells having a substantially planar base formed at least partially of an elastomeric membrane, with said elastomeric membrane having an upper surface treated to permit cell growth and attachment thereto by means of the incorporation at said upper surface of a substance selected from the group consisting of an amine, a carboxylic acid, or elemental carbon.

* * * * *